United States Patent [19]

Stemmle et al.

[11] Patent Number: 5,840,330
[45] Date of Patent: Nov. 24, 1998

[54] PROCESS FOR THE PREPARATION OF SHAPED, COMPRESSED CONTROLLED-RELEASE UNIT-DOSAGE FORMS, AND THE COMPRESSED UNIT-DOSAGE FORMS THUS OBTAINED

[75] Inventors: Berthold Stemmle, Burgdorf; Klaus Budde, Burgwedel; Alexander Wirl, Heuchelheim; Fritz Demmer, Hirschberg-Leutershausen, all of Germany

[73] Assignee: Boehringer Mannhelm GmbH, Mannheim, Germany

[21] Appl. No.: 357,143

[22] Filed: Dec. 15, 1994

Related U.S. Application Data

[63] Continuation of Ser. No. 955,705, Dec. 18, 1992, abandoned.

[51] Int. Cl.⁶ .................................................. A61K 9/20
[52] U.S. Cl. ..................... 424/464; 424/468; 424/469; 424/470; 424/484; 424/485; 424/488
[58] Field of Search .................................. 424/464, 468, 424/469, 470, 484, 485, 488

[56] References Cited

U.S. PATENT DOCUMENTS

| | | | |
|---|---|---|---|
| 3,629,393 | 12/1971 | Nakamoto et al. | 424/470 |
| 4,540,566 | 9/1985 | Davis et al. | 424/480 |
| 4,608,248 | 8/1986 | Knecht et al. | 424/427 |
| 5,075,114 | 12/1991 | Roche | 424/470 |
| 5,128,142 | 7/1992 | Mulligan et al. | 424/488 |
| 5,215,755 | 6/1993 | Roche et al. | 424/469 |

*Primary Examiner*—Melvyn I. Marquis
*Assistant Examiner*—Robert Harrison
*Attorney, Agent, or Firm*—Nikaido Marmelstein Murray & Oram, LLP

[57] ABSTRACT

Process for the preparation of shaped, compressed controlled-release unit-dosage forms from a therapeutic active substance exhibiting a self-retarding release that depends on the magnitude of the force used for the compression. The process gives unit-dosage forms for which the release of the active substance is highly uniform, reproducibly identical and largely linear. To achieve this, the active substance and an additive charge that inhibits or compensates for the self-retardation of its release are processed into particles in the first stage of production, so that the preliminary compressed objects made from these particles without any further additives exhibit a rapid release (in comparison with the required controlled release) over the range of the force of compression envisaged for the production of the unit-dosage form in question, after which the particles are compressed in the second stage of production with a release-retarding agent to obtain the unit-dosage forms. The invention also relates to the unit-dosage forms thus obtained.

29 Claims, 1 Drawing Sheet

PROCESS FOR THE PREPARATION OF SHAPED, COMPRESSED CONTROLLED-RELEASE UNIT-DOSAGE FORMS, AND THE COMPRESSED UNIT-DOSAGE FORMS THUS OBTAINED

This application is a continuation of application Ser. No. 07/955,705 filed Dec. 18, 1992, now abandoned.

The present invention relates to a process for the preparation of shaped, compressed controlled-release unit-dosage forms from a therapeutically active substance exhibiting self-retardation properties that vary with the force of compression, also to the unit-dosage forms thus obtained.

It is well known that "shaped, compressed unit-dosage forms" are employed for medical and veterinary purposes in many different versions. This term is primarily used to denote ordinary tablets, film-coated tablets and sugar-coated tablets, but the invention can also be utilized to make special types of therapeutic unit-dosage forms. However, tablets will be taken here as an example for the sake of simplicity, but without prejudice to the general applicability of the invention.

Controlled-release tablets are often devised to ensure a slow and steady release of the therapeutic active ingredient over a prolonged period of time. This can often increase the duration of action of a drug, or it can at least simplify its ingestion pattern for the patient.

It is particularly easy to slow down the release of a substance the activity of which is dependent on the pressure used in the compression. An example of such active substances is bezafibrate, a lipid-lowering drug that has become quite important in the treatment of elevated blood lipid levels. This substance forms needle-shaped crystals that can be compressed into controlled-release tablets and other solid unit-dosage forms without using any special release-retarding agents, the slowing-down of the release being adjusted here via the force of compression applied. The stronger this tabletting force, the slower the release of the active ingredient will be. This variation of the rate of release with the force of compression is noticeable even at relatively low values of about 10 $kN/cm^2$.

Further details about this active substance and suitable methods for its preparation are to be found in U.S. Pat. No. 3,781,328 and in German Patent Application DE-A 2,149,070.

Other active substances of this type are: 4-[2-(chlorobenzenesulphonylamino)-ethyl]-phenylacetic acid and 4-[2-(benzenesulphonylamino)ethyl]-phenoxyacetic acid, since the rate of the in vitro release of both depends to a considerable extent on the tabletting pressure employed, as a result of which their release is slowed down according to this pressure. These active substances have been described in detail in two European Patent applications (EP-A 31,954 and EP-A 4,011) and in two U.S. Pat. Nos. (Pat. No. 4,443,477 and Pat. No. 4,258,058).

A special advantage of these active substances with a self-retarding release is that they require only small amounts of additives, so that relatively large amounts of the active substance itself can be packed into a relatively small unit-dosage form.

Despite these favourable properties, however, the known controlled-release preparations of this type are not satisfactory in every respect. In particular, their release retardation shows rather large variations. This means that the production parameters must be controlled very accurately, and there is a greater risk that some of the output will have to be rejected for not having the required pharmaceutical properties.

However, it is desirable from the medical point of view to ensure that the release of the active ingredient is as uniform, reproducible, and linear as possible.

The aim of the present invention is therefore to improve these characteristics of the controlled-release preparations mentioned in the introduction. At the same time, the total amount of additives incorporated is to be increased as little as possible, so as to permit the production of compact unit-dosage forms with a high active-substance content.

To achieve this aim in a process of the type mentioned in the introduction, the active substance and an additive charge that inhibits or compensates for the self-retardation of the release of the active substance are converted into particles in the first stage of the production in such a way that (preliminary) compressed objects (slugs) prepared from this particulate matter without any further additives exhibit a rapid release (in comparison with the required slow release) over the range of values of the compression force envisaged for the production of the unit-dosage forms, after which the particles and a release-retarding additive are compressed into the required finished unit-dosage forms in the second stage of production.

The unit-dosage form according to the invention, which is composed of compacted particles containing a therapeutically active substance whose release retardation depends on the force of compression employed, and an outer phase containing some tabletting additives, is characterized in that the particles contain an additive charge that inhibits or compensates for the auto-retardation of the active substance in such a way that (preliminary) compressed objects, which are made from these particles without any further additives, exhibit a rapid release (in comparison with the required slow release) over the whole range of values envisaged for the force of compression, and in that the outer phase of the tablets contains a release-retarding agent.

The particulate matter prepared in the first stage of production is preferably a granulate, especially one obtained by wet granulation. However, it can also be made by other conventional methods, notably by dry granulation or by pelletizing in the usual manner. Pellets that are particularly suitable for the production of tablets are described in European Patent application EP-A 218,928.

The size of the particles prepared in the first stage of production can vary within wide limits. The most frequently occurring particle diameter d' in the RRSB mesh system is preferably between about 0.2 and 0.5 mm, and the particle sizes can range from about 0.01 mm to 2.0 mm.

The present Description will enable the expert to select suitable additives that satisfy the "release requirement," i.e. the above-mentioned relationship between the release of the active substance from the preliminary compressed objects made from the particles without any further additives and the required retardation of the release of the active substance from the unit-dosage form. In particular, the active substance can be processed with a large amount of hydrophilic additives such as sugars, sugar alcohols or polyethylene glycols. Alternatively, the first stage of production may involve the use of some additives with a large specific surface area, which act as a kind of wick in the tablets, facilitating the penetration of water or gastric juices into the tablet structure.

However, the procedures described below are particularly preferred, as they are specially suitable for the subject of the present invention and permit the use of very small amounts of additives.

The first stage of production preferably involves the use of a pharmaceutical tablet-disintegrating additive (Tablettenzerfallhilfsmittel) that is suitable for use with drugs and is normally employed in the pharmaceutical industry, such as those described in P. H. List and U. A. Muazzam: "Quellung—die treibende Kraft beim Tablettenzerfall" (=Swelling–the motive force behind the disintegration of tablets), Pharm. Ind., 41, No. 5(1979) 459 ff. These substances accelerate the disintegration of the aggregates into discrete individual particles (primary particles), three examples being a modified starch, a modified cellulose and cross-linked polyvinylpyrrolidone. For the sake of simplicity, these agents will be called here by their usual though less precise name of "disintegrants (Sprengmittel)".

In another preferred embodiment, the first stage of production involves the use of a wetting agent, preferably together with a water-soluble pharmaceutical binder. This is precisely the combination that ensures a release of the active substance that is particularly uniform, as well as being reproducible across different production batches of tablets.

Suitable additives, notably tablet disintegrants, wetting agents and water-soluble binders are specified in standard pharmaceutical reference works and especially in H. Sucker, P. Fuchs and P. Speiser (Eds.): "Pharmazeutische Technologie" (=Pharmaceutical Technology), published by Georg Thieme Verlag, Stuttgart, 1978.

BRIEF DESCRIPTION OF THE DRAWINGS

The invention is further elucidated by the experimental data given in the figures and tables enclosed, where:

FIG. 1 shows the rate of in vitro dissolution (in terms of % in the course of time in hours) for six different formulations of a controlled-release bezafibrate preparation in accordance with the prior art, all being in the form of tablets with a diameter of 11 mm. The force of compression varied as follows:

P1=10 kN (in the case of curves 1a and 1b),
P2=20 kN (in the case of curves 2a and 2b), and
P3=28 kN (in the case of curves 3a and 3b).

With each pair a and b, the bezafibrate used for curve a and that used for curve b differed in bulk volume (Schüttvolumen). In the case of curves a, the bulk volume was at its lower limit for controlled-release preparations (corresponding to a specific surface area of about 0.4 m²/g) and in the case of curves b, the bulk volume was at its upper limit for controlled-release preparations (corresponding to a specific surface area of about 0.9 m²/g).

Figure 1:
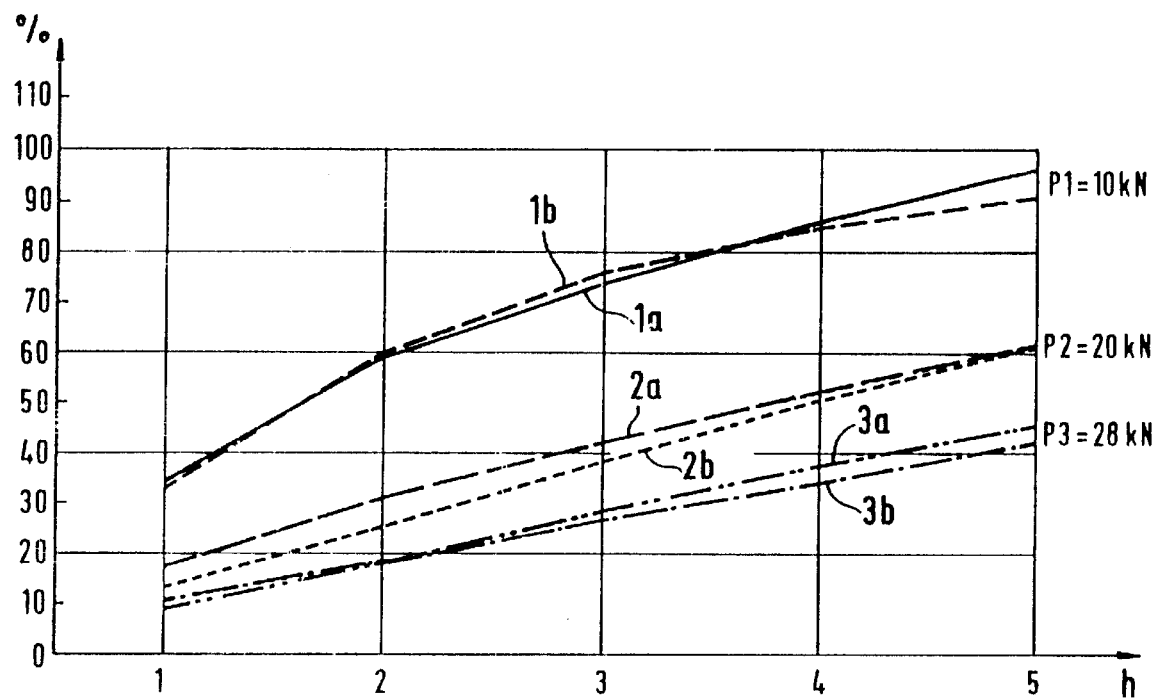
FIG. 1 shows a diagram for the in vitro release from unit-dosage forms of the prior art.

FIG. 1 clearly shows that the rate of in vitro dissolution of such controlled-release tablets known from the prior art varies with the force of compression to a large extent, while the bulk volume of bezafibrate has a very small influence on it.

Figure 2:
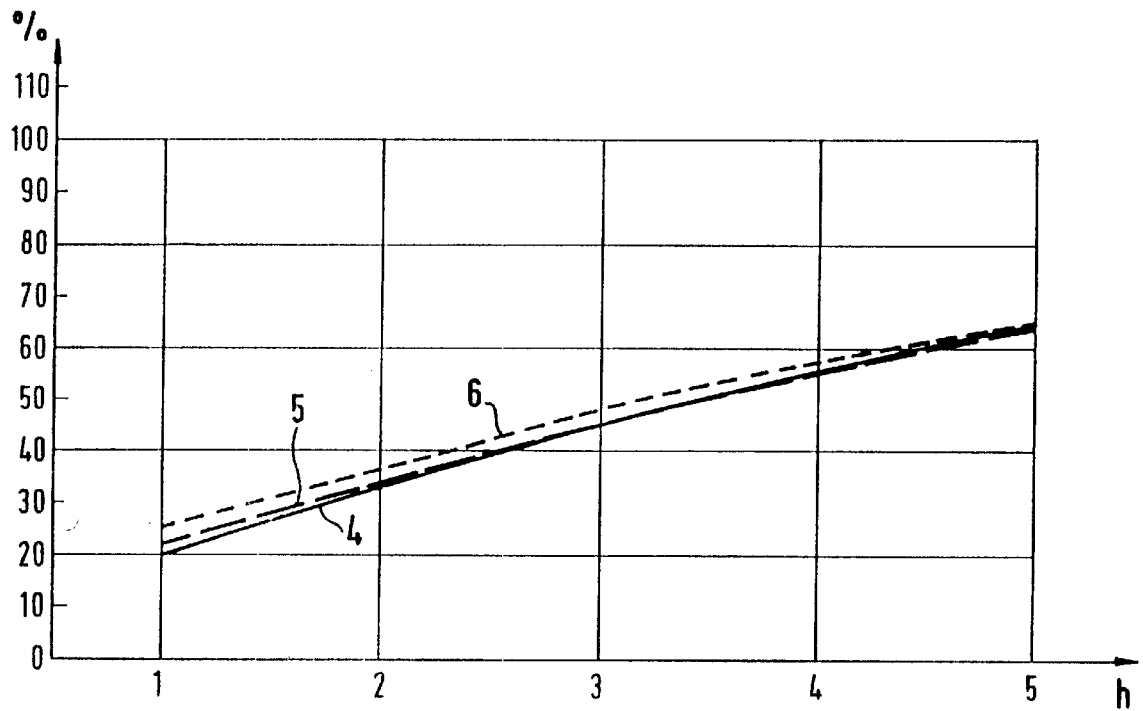
FIG. 2 shows a diagram for the in vitro release from unit-dosage forms according to the present invention.

FIG. 2 shows by contrast a corresponding diagram for the formulation according to the present invention, prepared as described in Example 7a. The tablets had the same size as in the case of FIG. 1 and were compressed under the same pressures: 10, 20 and 28 kN in the case of curves 4, 5 and 6, respectively. The rate of in vitro dissolution is seen to be virtually independent of the force of compression here and is practically linear. This pattern was also found to have excellent reproducibility across the different production batches.

Examples 1–4 and the corresponding Table 1 will help to explain the "release requirement." It will be recalled that this requirement stipulates that the particles prepared in the first stage of production should contain an additive charge inhibiting or compensating for the auto-retardation of the release of the active substance, so that the preliminary compressed objects obtained from the particles without the use of any further additives exhibit a rapid release (in comparison with required slow release) over the range of values of the compression force envisaged for the production of the unit-dosage forms.

In each of Examples 1–4, the specified constituents of a formulation for particulate matter suitable for tabletting ("granulate formulation") were mixed in the dry state and then compressed into unit-dosage forms with a diameter of 11 mm with the aid of a tablet machine operated at the usual speed. The usual tabletting additives (3 mg of highly dispersed silica and 10 mg of magnesium stearate) were admixed to the granulate in the dry state in order to improve the processing characteristics of the material, i.e. its flow properties and release from the die, but this had virtually no effect on the rate of in vitro dissolution.

The rate of in vitro release was determined under the following conditions, giving a measure of the release of the active substance.

Solvent: 1000 ml of Küster Thiel's phosphate buffer
pH: 6.8
Speed of the paddle stirrer: 90 rpm
Temperature: 37° C.

An in vitro method is generally convenient for checking whether a given formulation satisfies the release requirement, using a method that shows a good correlation with the in vivo release. The same in vitro model was of course used here for determining the release from the preliminary compressed objects as for determining the release from the finished unit-dosage forms with a controlled release.

EXAMPLE 1

| | |
|---|---|
| Bezafibrate | 400 mg |
| Mono- or oligosaccharide (here lactose D80) | 51 mg |
| Polyvinylpyrrolidone 25,000 | 15 mg |

This formulation contains an oligosaccharide that is customarily employed as a diluent in the formation of the granules in the usual way, but which also facilitates the compression of a granulate into tablets. Polyvinylpyrrolidone is a water-soluble polymer that is customarily employed as a binder in such granulate formulations.

This formulation therefore does not contain any additives having the specific purpose to inhibit or compensate for the self-retardation of the release of the active substance. The data in Table 1 show that the rate of in vitro dissolution is in fact very low and varies with the force of compression to a considerable extent. The extent of dissolution after 5 h amounts to 33% and 23%, being well below the figures required for a controlled-release preparation (see the Example corresponding to FIG. 2).

EXAMPLE 2

| | |
|---|---|
| Bezafibrate | 400 mg |
| Mono- or oligosaccharide (here lactose D80) | 51 mg |
| Sodium dodecyl sulphate (wetting agent) | 10 mg |

When low compressive forces are used, the wetting agent (sodium dodecyl sulphate) considerably increases the rate of in vitro dissolution, but the latter still varies greatly with the force of compression, and the mechanical properties of the compressed objects are not fully satisfactory either.

EXAMPLES 3A AND 3B

|  | 3A | 3B |
|---|---|---|
| Bezafibrate | 400 mg | 400 mg |
| Mono- or oligosaccharide (here mannitol) | 53 mg | 53 mg |
| Polyvinylpyrrolidone 25,000 | 15 mg | 15 mg |
| Sodium carboxymethyl starch | 4 mg | 8 mg |

These formulations contain the disintegrant sodium carboxymethyl starch in two concentrations. As the data in Table 1 show, this leads to an in vitro dissolution of the compressed products that is both quick and independent of the magnitude of the force of compression. The release requirement stipulated in the present invention is fully satisfied in the case of the products obtained in these Examples. It is also found that even a very small amount of the disintegrant—1% on the active substance—is sufficient for this purpose, and so the size of the tablets is virtually unchanged.

EXAMPLE 4

| Bezafibrate | 400 mg | 400 mg |
|---|---|---|
| Mono- or oligosaccharide (here lactose D80) | 51 mg | 51 mg |
| Polyvinylpyrrolidone 25,000 | 15 mg | 15 mg |
| Sodium dodecyl sulphate | 10 mg |  |
| Macrogol stearate 2500 |  | 10 mg |

These formulations contain both a water-soluble polymeric binder (polyvinylpyrrolidone) and a wetting agent, but whereas the formulation in Example 4A contains the anionic wetting agent sodium dodecyl sulphate, the formulation in Example 4B contains the non-ionic wetting agent Macrogol stearate 2500. The data in Table 1 show that the release requirement is satisfied by formulation 4A for all values used for the force of compression. In the case of formulation 4B, however, a barely sufficient dissolution of the compressed objects is obtained—and that only at relatively low values employed for the force of compression.

The following general conclusions can be drawn from Examples 1–4:

With the aid of relatively small quantities of additives which inhibit or compensate for self-retardation, it is possible to produce preliminary compressed objects from bezafibrate which display a rapid release (in comparison with the required controlled release) of the unit-dosage form at normal tablet-making pressures.

This can be achieved particularly effectively by the use of a disintegrant. Very good results can also be obtained with a combination of a water-soluble binder and a preferably anionic surfactant.

Examples 5–8 serve to demonstrate the effectiveness of the invention in conjunction with methylhydroxypropyl cellulose (MHPC) as the retardant.

In Examples 5–7A 400 mg bezafibrate are in each instance wet-granulated with a water-soluble binder and either a disintegrant or a surfactant in accordance with the above Examples 3B, 4A and 4B. The granulate is compressed together with the constituents listed as the outer phase to form tablets with a diameter of 11 mm. The in vitro release rate is observed as previously.

EXAMPLES 5, 6 AND 7A

|  | 5 | 6 | 7A |
|---|---|---|---|
| Granulate: |  |  |  |
| Bezafibrate | 400 mg | 400 mg | 400 mg |
| Lactose D80 |  | 53 mg | 51 mg |
| Mannitol | 53 mg |  |  |
| Polyvinylpyrrolidone 25,000 | 15 mg | 15 mg | 15 mg |
| Sodium carboxymethyl starch | 8 mg |  |  |
| Sodium dodecyl sulphate |  |  | 10 mg |
| Macrogol stearate 2500 |  | 10 mg |  |
| Outer phase: |  |  |  |
| MHPC K 100 LV | 51 mg | 49 mg | 51 mg |
| Highly dispersed silica | 3 mg | 3 mg | 3 mg |
| Magnesium stearate | 10 mg | 10 mg | 10 mg |

The results obtained with these formulations are listed in Table 2. These show that the release of the active substance is largely independent of the force of compression in all three cases. The release is similar in Examples 5 and 6, but formulation 5 has a higher crushing strength and a lower abrasion value.

Surprisingly, the granulate formulation that is found to be suitable but not so favourable in Examples 1–4 exhibits here a release that is particularly uniform, linear and independent of the force of compression when it contains both an anionic surfactant and a water-soluble polymeric binder. Furthermore, fully satisfactory mechanical properties are also obtained in this case. The fact that the rate of release shows only small variations is particularly advantageous; this is reflected in the coefficient of variation ("CV") given in brackets after the rate of in vitro dissolution in the tables. The dissolution behaviour of the formulation 7A is shown in FIG. 2.

This Example also demonstrates that the release requirement must not be interpreted in the sense that the rate of instantaneous dissolution of the preliminary compressed objects should be higher than that of the finished tablets over the entire period of the retarded dissolution. Thus, in the present case, the rate of instantaneous dissolution is virtually the same in both cases in the first hour for the higher compression forces, as can be seen by comparing the data for Example 4A in Table 1 with the data for Example 7A in Table 2.

However, the dissolution must be significantly different for the time interval typical of controlled-release preparations. In quantitative terms, the dissolution of the preliminary compressed object should be at least 1.5 times as advanced after three hours as that of the finished tablet.

Examples 7B–7E demonstrate the retarding action of various concentrations of methylhydroxypropylcellulose (MHPC) in a formulation that otherwise corresponds to that used in the preferred Example 7A:

| 7B | 7C | 7D | 7E |
|---|---|---|---|
| 31 mg | 41 mg | 71 mg | 101 mg |

The values listed in Table 2 show that, when MHPC is used in very small amounts (less than about 10% on the active substance), the release retardation varies with the force of compression. However, the data do not show the expected drop in the rate of in vitro dissolution with increasing force of compression, despite what is expected on the basis of the behaviour of the pure active ingredient itself. On the contrary, the tablets prepared at a higher force of compression dissolve faster.

At MHPC concentrations above the stated minimum, the release retardation can be set at will within a wide range.

To isolate the effect of the surfactant, a formulation similar to 7A but containing no surfactant, only a water-soluble polymer, was tested in the following Example.

EXAMPLE 8

| Granulate: | |
|---|---|
| Bezafibrate | 400 mg |
| Mono- or oligosaccharide (here lactose D80) | 51 mg |
| Polyvinylpyrrolidone | 15 mg |
| Outer phase: | |
| MHPC K 100 LV | 51 mg |
| Highly dispersed silica | 3 mg |
| Magnesium stearate | 10 mg |

The data in Table 2 show that the release retardation does not vary so much with the force of compression here, but this variation is still troublesome, and what is worse, the coefficient of variation has very high values, so the properties of the formulation do not have a good reproducibility.

Overall, particularly favourable effects are observed with a formulation that contains:

a water-soluble binder (especially polyvinylpyrrolidone) and an anionic surfactant (especially sodium dodecyl sulphate)

in the first stage of production (particulate matter), and a substance that forms a gel matrix (especially MHPC) as a release retarding agent ("retardant")

in the second stage of production (formulation of the outer phase). The quality of release retardation is better than expected on the basis of the dissolution properties of the preliminary tablets, so that a synergistic action can be postulated here, which is presumably due to an interaction between the anionic wetting agent and the MHPC.

However, the invention can also be used to advantage in its general form with other combinations of additives, and notably with other conventional release-retarding agents (retardants). Thus, sodium alginate has been found suitable in a series of experiments, and amongst the cellulose derivatives, sodium carboxymethyl cellulose can be used.

The water-soluble binder polyvinylpyrrolidone can be replaced by cellulose derivatives (e.g. low-viscosity methylhydroxypropyl celluloses and hydroxypropyl celluloses with a low degree of substitution) as well as by sugar esters and solid polyethylene glycols.

However, the possibilities are limited as regards the surfactants. Of the ionic ones, only sodium dodecyl sulphate is allowed to be used as a pharmaceutical additive. The non-ionic surfactant, on the other hand, can also be for example a Macrogol stearate (e.g. Macrogol 50 stearate), a Polysorbate (e.g. Polysorbate 80) or a polyoxyethylene—polyoxypropylene copolymer (e.g. Pluronic F 68).

So many pharmaceutical additives are available on the market that no rule can be given for the instant selection of either the additives to be used in the first stage of production (i.e. with the particles) or the release-retarding agents to be used in the second stage of production (i.e. with the outer phase). On the basis of the information contained in the present description, however, the expert will be able to find the right additives from the available range and test them for their suitability by simple experiments.

However, amongst the various types of methylhydroxypropylcellulose available on the market, a product with the following values has been found to be particularly suitable:

amount of hydroxypropyl:<9% average molecular weight:about 26,000 mean viscosity of a 2% solution at 20° C.:0.1 Pa.sec.

TABLE 1

| Example No. | Force of compression [KN] | Crushing strength [N] | Abrasion [%] | Rate of in vitro dissolution (with the coefficients of variation - CV - given in brackets) [%] | | | | |
|---|---|---|---|---|---|---|---|---|
| | | | | 1 [h] | 2 [h] | 3 [h] | 4 [h] | 5 [h] |
| 01 | 10 | 129 | 0,55 | 6 (5,8) | 8 (9,4) | 16 (6) | 20 (7,5) | 33 (9,5) |
| | 20 | 144 | 0,52 | — | — | — | — | — |
| | 28 | 153 | 0,54 | 4 (13,9) | 11 (4,9) | 12 (5,7) | 13 (11,5) | 23 (8,8) |
| 02 | 10 | 54 | seal | 35 (65,5) | 61,0 (38,9) | 71,0 (29,3) | 76,0 (25,7) | 79,0 (23,5) |
| | 20 | 57 | seal | 12 (6,4) | 19,0 (6,1) | 24,0 (7,2) | 28,0 (8,4) | 31,0 (9,1) |
| | 28 | 58 | seal | 12 (2,3) | 19,0 (2,6) | 23,0 (2,9) | 26,0 (3,6) | 29,6 (3,9) |
| 03A | 10 | 109 | 0,45 | 97 90,9) | 98,0 (0,7) | 98,0 (0,9) | 99,0 (0,7) | 100,0 (0,7) |
| | 20 | 167 | 0,39 | 94 (1,6) | 99,0 (0.8) | 99,0 (0,7) | 100,0 (0,8) | 100,0 (0,9) |
| | 28 | — | — | — | — | — | — | — |
| 03B | 10 | 106 | — | 98 (1,0) | 98 (1,2) | 98 (1,2) | 98 (1,2) | 99 (0,9) |
| | 20 | 164 | 0,3 | 97 (1,0) | 97 (1,0) | 98 (1,0) | 98 (1,1) | 98 (1,0) |
| | 28 | 165 | — | — | — | — | — | — |
| 04A | 10 | 136 | 0,55 | 70 (4,7) | 99 (1,0) | 100 (0,7) | | |
| | 20 | 188 | 0,62 | 21 (4,0) | 60 (14,2) | 100 (3,9) | | |
| | 28 | 197 | 0,51 | 20 (3,8) | 61 (7,2) | 96 (1,0) | | |
| 04B | 10 | 80 | 0,81 | 20 (14,2) | 49,0 (21,1) | 76,0 (20,5) | 91,0 (8,9) | 98,0 (1,9) |
| | 20 | 94 | 0,69 | 16 (3,4) | 29,0 (4,4) | 41,0 (6,2) | 53,0 (8,7) | 64,0 (10,0) |
| | 28 | 100 | 0,55 | 16 (3,8) | 29,0 (2,3) | 40,0 (1,9) | 51,0 (2,0) | 62,0 (2,3) |

TABLE 2

| Example No. | Force of compression [KN] | Crushing strength [N] | Abrasion [%] | Rate of in vitro dissolution (with the coefficients of variation - CV - given in brackets) [%] | | | | |
|---|---|---|---|---|---|---|---|---|
| | | | | 1 [h] | 2 [h] | 3 [h] | 4 [h] | 5 [h] |
| 05 | 10 | 163 | 0,30 | 38,0 (10,1) | 54,0 (8,2) | 71 (8,7) | 84,0 (9,3) | 96,0 (6,9) |
| | 20 | 231 | 0,30 | 48,0 (16,7) | 65,0 (13,1) | 75 (11,6) | 85,0 (10,5) | 97,0 (5,7) |
| | 28 | 262 | 0,30 | 44,0 (18,3) | 59,0 (14,2) | 71 (13,4) | 81,0 (10.8) | 90,0 (8,5) |
| 06 | 10 | 52 | 0,6 | 46,0 (9,4) | 63,0 (9,2) | 78 (9,7) | 91,0 (8,7) | 100,0 (4,9) |
| | 20 | 95 | 0,4 | 54,0 (9,8) | 67,0 (8,7) | 78 (7,2) | 89,0 (8,8) | 97,0 (6,2) |
| | 28 | 111 | 0,4 | 59,0 (25,9) | 71,0 (24,6) | 80 (17,7) | 87,0 (12,7) | 95,0 (9,5) |
| 07A | 10 | 98 | 0,7 | 20,0 (6,6) | 33,0 (5,1) | 45,0 (5,1) | 55,0 (5,5) | 65,0 (5,6) |
| | 20 | 160 | 0,3 | 22,0 (5,9) | 34,0 (3,6) | 45,0 (4,4) | 55,0 (3,6) | 64,0 (4,3) |
| | 28 | 180 | 0,5 | 25,0 (6,9) | 36,0 (6,5) | 48,0 (6,0) | 57,0 (9,8) | 65.0 (6,5) |
| 07B | 10 | 146 | 0,5 | 35,0 (17,1) | 54,0 (15,6) | 72,0 (11,6) | 89,0 (11,7) | 96,0 (7,4) |
| | 20 | 171 | 0,4 | 61,0 (15,7) | 88,0 (14,8) | 94,0 (9,5) | 98,0 (4,9) | 100,0 (2,2) |
| | 28 | 200 | 0,4 | 66,0 (4,3) | 91,0 (6,1) | 99,0 (3,6) | 101,0 (1,1) | 102,0 (0.8) |
| 07C | 10 | 121 | 0,3 | 24,0 (7,0) | 38,0 (5,2) | 49,0 (4,5) | 59,0 (4,4) | 69,0 (4,5) |
| | 20 | 168 | — | 45,0 (14,7) | 56,0 (12,0) | 66,0 (9,2) | 76,0 (10,7) | 85,0 (10,5) |
| | 28 | 164 | 0,2 | 49,0 (13,2) | 60,0 (11,8) | 68,0 (10,8) | 77,0 (13,0) | 86,0 (11,9) |
| 07D | 10 | 136 | 0,2 | 14,0 (29,8) | 29,0 (20,2) | 43,0 (18,0) | 53,0 (18,1) | 63,0 (17,7) |
| | 20 | 195 | 0,3 | 15,0 (8,2) | 30,0 (7,1) | 45,0 (7,2) | 56,0 (6,7) | 66,0 (6,1) |
| | 28 | 208 | 0,2 | 16,0 (10,4) | 31,0 (8,4) | 45,0 (10,1) | 56,0 (9,2) | 67,0 (8,5) |
| 07E | 10 | 133 | 0,2 | 10,0 (21,1) | 22,0 (18,1) | 34,0 (16,0) | 44,0 (15,2) | 53,0 (14,5) |
| | 20 | 206 | 0,2 | 10,0 (23,5) | 22,0 (21,8) | 34,0 (20,2) | 44,0 (18,1) | 53,0 (16,9) |
| | 28 | 229 | 0,2 | 10,0 (7,7) | 22,0 (6,2) | 34,0 (6,0) | 45,0 (5,7) | 55,0 (5,4) |
| 08 | 10 | 114 | 0,1 | 33,0 (23,3) | 50,0 (20,1) | 63,0 (18,7) | 75,0 (17,4) | 85,0 (15,8) |
| | 20 | 170 | 0,1 | 31,0 (21,3) | 55,0 (19,2) | 69,0 (18,2) | 81,0 (17,7) | 89,0 (17,0) |
| | 28 | 180 | 0,2 | 34,0 (19,2) | 69,0 (13,5) | 85,0 (8,9) | 94,0 (5,7) | 100,0 (3,4) |

We claim:

1. Process for the preparation of shaped, compressed, controlled-release unit-dosage forms from a therapeutic active substance exhibiting self-retardation properties of release such that unit-dosage forms compressed from such active substance without release retarding agent provide controlled-release behavior, comprising:

(1) converting the active substance and a additive charge that inhibits or compensates for the self-retardation properties of said active substance by granulation into granulate particles wherein said additive charge is such that compressed objects made from said granulate particles with the same pressure which is used for the production of the unit-dosage forms without any further additives exhibit a release which is more rapid than the release of said controlled-release unit-dosage forms, and then (2) compressing said granulate particles with a release-retarding agent such that said granulate particles form an inner phase and said release-retarding agent is contained in an outer phase distinct from said inner phase, thereby forming the unit-dosage forms.

2. A process as recited in claim 1, wherein said additive charge comprises a pharmaceutical tablet disintegrant, a wetting agent, or a pharmaceutical binder.

3. A process as recited in claim 2, wherein said tablet disintegrant is incorporated in a concentration of 0.10–10 wt-%, calculated on the amount of active substance.

4. A process as recited in claim 2, wherein said wetting agent is an anionic surfactant.

5. A process as recited in claim 2, wherein said wetting agent is used in an amount of 0.10–10 wt-%, calculated on the quantity of the active substance.

6. A process as recited in claim 2, wherein said binder is water-soluble and is incorporated in an amount of 0.1–10 wt-%, calculated on the quantity of the active substance.

7. A process as recited in claim 1, wherein said release-retarding agent is a hydrogel-forming-substance and is used in an amount of 5–40 wt-%, calculated on the quantity of the active substance, or an alginate.

8. A process as recited in claim 7, wherein said hydrogel-forming-substance is a cellulose derivative with a molecular weight of less than 50,000 and a hydroxypropyl content of less than 9%.

9. A process as recited in claim 3, wherein said tablet disintegrant is incorporated in a concentration of 0.25–5 wt. %, calculated on the amount of active substance.

10. A process as recited in claim 2, wherein said wetting agent is sodium dodecyl sulphate.

11. A process as recited in claim 5, wherein said wetting agent is used in an amount of 0.5–5 wt. %, calculated on the quantity of the active substance.

12. A process as recited in claim 6, wherein said binder is incorporated in an amount of 0.25–6 wt. %, calculated on the quantity of the active substance.

13. A process as recited in claim 8, wherein said hydrogel-forming-substance is a methylhydroxypropyl cellulose or a sodium carboxymethyl cellulose.

14. A process as recited in claim 7, wherein said release-retarding agent is sodium alginate.

15. A process as recited in claim 1, wherein said active substance is bezafibrate.

16. A shaped, compressed controlled-release unit-dosage form having an inner phase and an outer phase which is distinct from said inner phase, said inner phase comprising bezafibrate and an additive charge, said bezafibrate exhibiting self-retardation properties of release such that unit-dosage forms compressed from bezafibrate without release retarding agents provide controlled release behavior, said additive charge being a material that inhibits or compensates for the self-retardation properties of said bezafibrate, such that compressed objects made from only said bezafibrate and said additive charge would exhibit release which is more rapid than said controlled-release unit-dosage form, over the range of the force of compression used for the production of the unit-dosage form, said outer phase comprising a release-retarding agent.

17. A shaped, compressed controlled-release unit-dosage form as recited in claim 16, wherein said additive charge comprises a pharmaceutical tablet disintegrant, a wetting agent or a pharmaceutical binder.

18. A shaped, compressed controlled-release unit-dosage form as recited in claim 17, wherein said tablet disintegrant is incorporated in a concentration of 0.1–10 wt-%, calculated on the amount of said bezafibrate.

19. A shaped, compressed controlled-release unit-dosage form as recited in claim 17, wherein said wetting agent is an anionic surfactant.

20. A shaped, compressed controlled-release unit-dosage form as recited in claim 17 wherein said wetting agent is used in an amount of 0.1–10 wt-%, calculated on the quantity of said bezafibrate.

21. A shaped, compressed controlled-release unit-dosage form as recited in claim 17, wherein said binder is water-soluble and is incorporated in an amount of 0.1–10 wt-%, calculated on the quantity of said bezafibrate.

22. A shaped, compressed controlled-release unit-dosage form as recited in claim 16, wherein said release-retarding agent is a hydrogel-forming substance and is used in an amount 5–40 wt-%, calculated on quantity of said bezafibrate, or said release-retarding agent is an alginate.

23. A shaped, compressed controlled-release unit-dosage form as recited in claim 22, wherein said hydrogel-forming-substance is a cellulose derivative with a molecular weight of less than 50,000 and a hydroxypropyl content of less than 9%.

24. A shaped, compressed controlled-release unit-dosage form as recited in claim 18, wherein said tablet disintegrant is incorporated in a concentration of 0.25–5 wt. %, calculated on the amount of said bezafibrate.

25. A shaped, compressed controlled-release unit-dosage form as recited in claim 17, wherein said wetting agent is sodium dodecyl sulphate.

26. A shaped, compressed controlled-release unit-dosage form as recited in claim 20, wherein said wetting agent is used in an amount of 0.5–5 wt. %, calculated on the quantity of said bezafibrate.

27. A shaped, compressed controlled-release unit-dosage form as recited in claim 21, wherein said binder is incorporated in an amount of 0.25–6 wt. %, calculated on the quantity of said bezafibrate.

28. A shaped, compressed controlled-release unit-dosage form as recited in claim 23, wherein said hydrogel-forming-substance is a methylhydroxypropyl cellulose or a sodium carboxymethyl cellulose.

29. A shaped, compressed controlled-release unit-dosage form as recited in claim 22, wherein said release-retarding agent is sodium alginate.

* * * * *